US012715827B2

(12) United States Patent
Feinstein

(10) Patent No.: US 12,715,827 B2
(45) Date of Patent: Aug. 25, 2026

(54) GREEN METHANOL PRODUCTION

(71) Applicant: ZoneFlow Reactor Technologies, LLC, Windsor, CT (US)

(72) Inventor: Jonathan Jay Feinstein, Windsor, CT (US)

(73) Assignee: ZoneFlow Reactor Technologies, LLC, Windsor, CT (US)

( * ) Notice: Subject to any disclaimer, the term of this patent is extended or adjusted under 35 U.S.C. 154(b) by 583 days.

(21) Appl. No.: 18/314,682

(22) Filed: May 9, 2023

(65) Prior Publication Data

US 2023/0271905 A1 Aug. 31, 2023

Related U.S. Application Data

(63) Continuation of application No. PCT/US2021/072386, filed on Nov. 12, 2021.
(Continued)

(51) Int. Cl.
*C07C 29/151* (2006.01)
*B01J 19/00* (2006.01)
(Continued)

(52) U.S. Cl.
CPC ....... *C07C 29/1518* (2013.01); *B01J 19/0013* (2013.01); *B01J 19/245* (2013.01);
(Continued)

(58) Field of Classification Search
None
See application file for complete search history.

(56) References Cited

U.S. PATENT DOCUMENTS 4,238,403 A * 12/1980 Pinto ........................ C10G 9/00
518/704
5,079,267 A 1/1992 Kao et al.
(Continued)

FOREIGN PATENT DOCUMENTS

DE 3244302 A1 5/1984
JP 1986-030542 A 2/1986
(Continued)

OTHER PUBLICATIONS

Machine translation JPH10259148A, Sep. 29, 1998, pp. 1-14 (Year: 1998).*

*Primary Examiner* — Medhanit W Bahta
(74) *Attorney, Agent, or Firm* — Knobbe, Martens, Olson & Bear, LLP

(57) ABSTRACT

Steam reforming, water separation, and hydrogen separation by membrane can be performed sequentially on a mixture of steam and a hydrocarbon. A hydrogen-rich permeate stream from the hydrogen membrane can be used as fuel for combustion heating, leaving a retentate mixture of a prescribed ratio of hydrogen to oxides of carbon. The retentate can be compressed and synthesized to methanol in a methanol synthesis reactor. The synthesized methanol can be separated into a methanol-rich stream and a tail gas stream containing the remaining outlet gas from the synthesis reactor. The methanol-rich stream can be refined. The tail gas stream can be divided into a methanol loop recycle stream, an SMR recycle stream, and a nitrogen purge stream. The methanol loop recycle stream is compressed and recycled to the methanol synthesis reactor. The SMR recycle stream is recycled as feedstock to the reformer. The nitrogen purge stream is combusted in a burner. Carbon dioxide may be separated from combustion products and sequestered.

14 Claims, 2 Drawing Sheets

Related U.S. Application Data

(60) Provisional application No. 63/113,844, filed on Nov. 14, 2020.

(51) Int. Cl.

| | |
|---|---|
| ***B01J 19/24*** | (2006.01) |
| ***C01B 3/34*** | (2006.01) |
| ***C01B 3/501*** | (2026.01) |
| ***C07C 29/80*** | (2006.01) |

(52) U.S. Cl.

CPC ................ *C01B 3/34* (2013.01); *C01B 3/501* (2013.01); *C07C 29/80* (2013.01); *B01J 2208/00504* (2013.01); *C01B 2203/0233* (2013.01); *C01B 2203/0405* (2013.01); *C01B 2203/061* (2013.01); *C01B 2203/0822* (2013.01)

(56) References Cited

U.S. PATENT DOCUMENTS

| | | | | | |
|---|---|---|---|---|---|
| 5,998,489 | A | * | 12/1999 | Kobayashi | C07C 29/1518 518/700 |
| 6,159,395 | A | * | 12/2000 | Early | C07C 29/1518 252/375 |
| 6,191,174 | B1 | | 2/2001 | Early et al. | |
| 6,218,439 | B1 | * | 4/2001 | Kobayashi | C07C 29/1518 518/703 |
| 6,444,712 | B1 | | 9/2002 | Janda | |
| 6,495,610 | B1 | | 12/2002 | Brown | |
| 6,706,770 | B2 | | 3/2004 | Patel et al. | |
| 9,950,975 | B2 | | 4/2018 | Steynberg et al. | |
| 9,969,666 | B1 | | 5/2018 | Roesch et al. | |
| 2011/0269854 | A1 | | 11/2011 | Wynn et al. | |
| 2014/0163121 | A1 | | 6/2014 | Allam | |

FOREIGN PATENT DOCUMENTS

| | | | | | |
|---|---|---|---|---|---|
| JP | 1998-259148 | A | | 9/1998 | |
| JP | H10259148 | A | * | 9/1998 | |
| JP | 2007-320865 | A | | 12/2007 | |
| JP | 2014-156379 | A | | 8/2014 | |
| WO | WO 2020/159657 | | | 8/2020 | |
| WO | WO-2020249923 | A1 | * | 12/2020 | C07C 29/1518 |

* cited by examiner

FEED STOCK
deS
SYNTHESIS REACTOR
DISTILLATION
METHANOL /WATER
DISTILLATION
AIR
STACK
WATER KNOCK OUT
WATER OUT
FIN FAN
BFW

GREEN METHANOL PRODUCTION

CROSS-REFERENCE TO RELATED APPLICATIONS

This application is a continuation of International Application No. PCT/US2021/072386, filed Nov. 12, 2021, entitled GREEN METHANOL PRODUCTION, which claims the benefit of U.S. Provisional Application Ser. No. 63/113,844, filed Nov. 14, 2020, entitled GREEN METHANOL PRODUCTION, both of which are incorporated by reference herein in their entirety.

FIELD

The present disclosure relates to systems and methods for the production of methanol via steam reforming and catalytic synthesis.

SUMMARY

In a first aspect, a method of producing methanol comprises reforming a feed comprising steam and at least one hydrocarbon in a steam reforming unit to produce a syngas comprising hydrogen and one or more oxides of carbon; separating the syngas into a hydrogen-rich stream and a second stream in a hydrogen separation unit; processing the second stream in a synthesis reactor to form an outlet stream comprising methanol; and separating the outlet stream into a methanol-rich stream and a methanol-poor tail gas stream. A first portion of the tail gas stream is recycled to the synthesis reactor and a second portion of the tail gas stream is recycled to form a portion of the feed.

In some embodiments, the hydrogen separation unit comprises a membrane.

In some embodiments, the method further comprises combusting at least a portion of the hydrogen-rich stream to provide heat to the steam reforming unit.

In some embodiments, the volume ratio of hydrogen to oxides of carbon in the second stream is between 1.8/1.0 and 2.8/1.0.

In some embodiments, the volume ratio of hydrogen to oxides of carbon in the second stream is approximately 2.5/1.0.

In some embodiments, a third portion of the tail gas stream is separated into a fuel stream.

In some embodiments, the method further comprises combusting at least a portion of the fuel stream to form combustion products and to provide heat to the steam reforming unit.

In some embodiments, the combustion products contain carbon dioxide.

In some embodiments, the method further comprises separating and sequestering at least a portion of the carbon dioxide from the combustion products.

In some embodiments, the method further comprises sequestering the separated carbon dioxide.

In some embodiments, the outlet stream is separated in a distillation column.

In some embodiments, the method further comprises pressurizing the second stream in a compressor.

In some embodiments, the second stream enters the synthesis unit at a pressure greater than 50 bar.

In some embodiments, the method further comprises preheating at least a portion of the feed against at least a portion of the outlet stream.

In some embodiments, the second portion of the tail gas stream is separated in a tail gas separating unit into a steam reforming recycle stream containing a relatively lower concentration of inert gases and a purge stream containing a relatively higher concentration of inter gases, and wherein the steam reforming recycle stream is recycled to the steam reforming unit.

In some embodiments, the purge stream is combusted to provide heat.

In a second aspect, a methanol production system comprises a steam reforming unit configured reform a feed comprising steam and at least one hydrocarbon to produce a syngas comprising hydrogen and one or more oxides of carbon; a hydrogen separation unit configured to separate the syngas into a hydrogen-rich stream and a second stream; a synthesis reactor configured to process the second stream to form an outlet stream comprising methanol; and a distillation column configured to separate the outlet stream into a methanol-rich stream and a methanol-poor tail gas stream. The distillation column is connected to one or more lines connected to recycle a first portion of the tail gas stream to the synthesis reactor and to recycle a second portion of the tail gas stream to form a portion of the feed.

In some embodiments, the system further comprises at least one compressor configured to pressurize the second stream between the hydrogen separation unit and the synthesis reactor.

In some embodiments, the system further comprises a furnace having a burner configured to combust the hydrogen-rich stream to heat the steam reforming unit.

In some embodiments, the system further comprises a turbo expander connected to receive at least some of the second portion of the tail gas stream.

In some embodiments, the hydrogen separation unit comprises a membrane.

In some embodiments, the system further comprises one or more heat exchangers disposed to preheat at least a portion of the feed against at least a portion of the outlet stream.

In some embodiments, the system further comprises a carbon dioxide scrubber configured to remove carbon dioxide from at least a portion of the methanol-poor tail gas stream for sequestration.

In some embodiments, the system further comprises a tail gas separating unit configured to separate the second portion of the tail gas stream into a steam reforming recycle stream containing a relatively lower concentration of inert gases and a purge stream containing a relatively higher concentration of inert gases, and wherein the steam reforming recycle stream is recycled into the steam reforming unit.

In some embodiments, the purge stream is combusted to provide heat.

DETAILED DESCRIPTION

Figure 1:
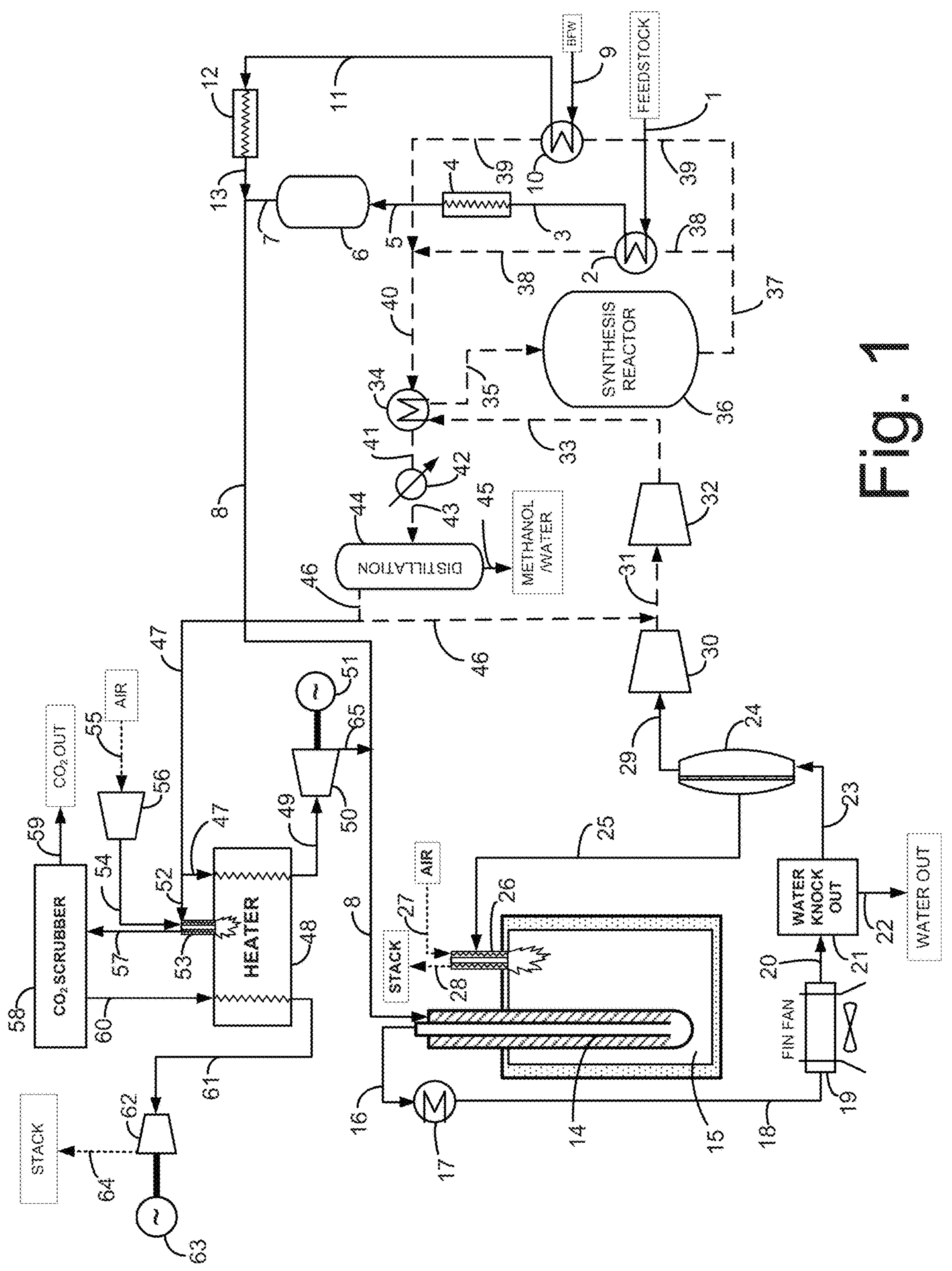
FIG. 1 schematically illustrates a methanol production unit in accordance with the present technology.

Steam methane reforming (SMR) processes include reacting a hydrocarbon feed with steam and/or carbon dioxide over a catalyst to produce syngas, a mixture of hydrogen and one or more oxides of carbon. A methanol synthesis unit may be fed with such a syngas to produce methanol. The syngas from an SMR unit often contains a relatively high ratio of hydrogen to carbon oxides (e.g., CO and/or $CO_2$), for example, of 3/1 to 4/1, or higher. However, a lower ratio, for example, about 2.5/1 can be advantageous.

A synthesis unit (e.g., containing a synthesis reactor, a catalytic reactor, or the like) may be in the form of a loop wherein the feedstock is only incrementally synthesized to methanol in a single pass and can be recirculated through the synthesis reactor multiple times in commercial practice. In each pass, makeup syngas from the SMR may be added. The makeup syngas may be generated at the SMR at a relatively low pressure (e.g., less than 40 bar), and can be pressurized and added to the returns or tail gas from the previous circulation or pass through the synthesis unit. The combined gas can be further pressurized (e.g., to pressures exceeding 50 bar) and the temperature can be adjusted to cause the syngas to enter the catalytic reactor at an optimal temperature for the incremental conversion performed.

The methanol synthesized in the catalytic reactor can be separated from the other tail gas constituents, which may include $CH_4$, $CO_2$, CO, $H_2$, and/or $N_2$, from the methane synthesis reactor as a tail gas. Some of the tail gas can be recycled within the synthesis loop between the two mentioned pressurization stations, part can be recycled to the feed or steam entering the steam reforming unit to further convert methane to hydrogen and oxides of carbon and prevent carbon contained in it from entering the combustion system, and part can be sent as fuel to fire the steam reformer furnace, effectively purging accumulated nitrogen from the loop.

Certain prior art methanol production methods may perform some amount of partial oxidation of hydrocarbon feedstock with refined oxygen to lower the ratio of hydrogen to oxides of carbon fed to the synthesis loop. This practice, while balancing the inlet requirements to the synthesis loop, requires an air separation unit, substantially adding to the capital, costs, and $CO_2$ emissions associated with the generation of electricity used in the air separation unit.

It would be desirable to lower the ratio of hydrogen to oxides of carbon fed to the synthesis loop from that of existing systems, without using an air separation plant. It would also be desirable to emit less carbon, for example, in the form of carbon monoxide or carbon dioxide from the process. It would further be desirable to cause more of the carbon in the feedstock to the SMR to become part of the methanol produced, rather than part of the carbon dioxide emissions. The present technology can accomplish some or all of the above objectives and others that will be manifest to a reader reasonably skilled in the art, guided by the instant disclosure.

In some embodiments, a mixed feed of steam and a feedstock hydrocarbon (or other feedstock containing hydrogen and carbon) is reformed in a steam reforming unit to form syngas containing hydrogen and oxides of carbon. The syngas can be cooled. Condensed water may be separated from the cooled syngas.

The dehumidified syngas can be separated in a hydrogen separating unit into a hydrogen-rich or permeate stream, and a second or retentate stream containing the remaining constituents of the syngas. According to some embodiments, the hydrogen-rich stream may contain at least 80%, at least 90%, and in some cases at least 95% hydrogen by volume. The volume ratio of hydrogen to the oxides of carbon, such as carbon monoxide and carbon dioxide, in the second or retentate stream can be adjusted, for example, to between 1.8/1.0 and 2.8/1.0 and in some cases to about 2.5/1.0 by the removal of the hydrogen-rich stream.

The hydrogen separation unit may be of any kind, such as a pressure swing adsorption unit, a distillation column, or other hydrogen separation unit, and can be a membrane separation unit with greater permeability to hydrogen than to the other species in the syngas. In an example implementation including a membrane separation unit, the back pressure of the hydrogen-rich permeate stream may be used to control the flow of permeate and thereby to adjust the ratio of hydrogen to oxides of carbon in the retentate to a prescribed ratio suitable for methanol synthesis.

The hydrogen-rich stream or permeate can be combusted as fuel for heating the reforming furnace, a boiler, the feedstock, or any other heating function within or outside the methanol production unit comprising the steam reforming unit, a methanol synthesis unit, and/or a methanol separation unit.

The retentate can be compressed to the approximate pressure of the tail gas from the synthesis loop and mixed as makeup gas with that tail gas. The mixture of makeup gas and tail gas can be compressed to a pressure suitable for the methanol synthesis reactor inlet, for example, at least 50 bar in some embodiments. The temperature of the mixture can be adjusted to a temperature suitable for the methanol synthesis reactor inlet and conveyed into the methanol synthesis reactor wherein the mixture is at least partially converted to methanol. Outlet gas from the synthesis reactor can be cooled and separated, such as by distillation or other means, into a methanol-rich stream and the tail gas stream. The methanol-rich stream may be further refined to methanol of a predetermined purity.

In some embodiments, the tail gas stream can be separated into three streams. A first tail gas stream can be mixed with the retentate or makeup syngas from the steam reforming unit and recirculated to the methanol synthesis unit. A second tail gas stream can be mixed with makeup feedstock and steam to the steam reforming unit and reformed in the reformer to produce syngas. A third tail gas stream can be conveyed to a burner wherein it is combusted with an oxidant such as air to provide heat for heating a load such as the examples of preheating feedstock to the reformer, raising steam, or heating the mixed feed in the steam reformer. Flue gas from the burner fed with tail gas may be optionally scrubbed of carbon dioxide by any means such as absorption by amine, creating a $CO_2$-rich stream and an effluent stream containing the remainder of the flue gas constituents. The $CO_2$-rich stream may be compressed and sequestered. For the purposes of the present disclosure, sequestration means isolation from the environment or atmosphere, whether by storage or by use or consumption in the production of a product.

The flow rate of the third tail gas stream, constituting a nitrogen purge stream in some embodiments, can be adjusted to prevent the nitrogen content of the tail gas from exceeding a predetermined concentration. The flow rate of the second tail gas stream or SMR recycle stream can be adjusted to prevent the methane content of the tail gas from exceeding a predetermined concentration.

Referring now to FIG. 1, an example methanol production unit implementing green methanol production aspects of the present technology will be described. It will be understood that FIG. 1 illustrates only an example embodiment of the present technology, and the green methanol production aspects of the present technology may equally be implemented in other methanol production unit configurations using the current disclosure as a guide. As shown in FIG. 1, line 1 conveys a hydrocarbon feedstock to a heat exchanger 2. The hydrocarbon feedstock can advantageously be natural gas or can be another hydrocarbon. In some embodiments, the hydrocarbon feedstock is a liquid, and is heated to be a gas or vapor. In some embodiments, the hydrocarbon feedstock is introduced as a gas. The feedstock in line 1 is preheated against gas in line 38 in the heat exchanger 2. The gas in line 38 can be a flue gas from a methane synthesis unit (described below), or from another process or from another component of the system.

Line 3 conveys the preheated feedstock from the heat exchanger 2 to a heater 4 wherein the preheated feedstock is further preheated to a temperature suitable for desulfurization. Line 5 conveys the preheated feedstock from the heater 4 to a desulphurization unit 6 wherein the feedstock is desulphurized. Line 7 conveys the desulphurized feedstock from the desulphurization unit 6 to line 8 wherein the feedstock mixes with steam from line 13.

Line 9 conveys boiler feed water to a heat exchanger 10 wherein the boiler feed water is preheated against gas in line 39. In some embodiments, the gas in line 39 can be a flue gas, can be the outlet/flue gas from a methane synthesis unit, or can be from another source. Line 11 conveys the preheated boiler feed water from the heat exchanger 10 to a boiler 12 wherein the preheated boiler feed water is raised to steam. Line 13 conveys the steam from the boiler 12 to line 8 wherein the steam mixes with the feedstock from line 7 to form a mixed feed, for example, comprising desulphurized hydrocarbons and steam.

Line 8 conveys the mixed feed from lines 7 and 13 to a steam reforming reactor 14 wherein the mixed feed is converted to a syngas containing hydrogen and oxides of carbon. The steam reforming reactor 14 is heated by a furnace 15. The steam reforming reactor 14 can be a steam reforming reactor such as those described in U.S. application Ser. No. 16/920,562, filed Jul. 3, 2020, entitled "Bayonet Catalytic Reactor," the entire contents of which are hereby incorporated by reference. In some embodiments, the steam reforming reactor can be another type of steam reforming reactor.

Line 16 conveys the syngas from the steam reforming reactor 14 to a heat exchanger 17, wherein the syngas is cooled against a stream to be heated. The stream to be heated may be any of streams 1, 3, 9, 11, 47, 60, 26, 54, or 33 or another stream or fluid. Line 18 conveys the cooled syngas from the heat exchanger 17 to a fin fan 19.

In fin fan 19, or other similar apparatus for cooling the syngas, the syngas is cooled against ambient air or water, and some of the steam in the syngas condenses. Line 20 conveys the cooled syngas to a water knock out unit 21 wherein the condensed steam (in the form of liquid water) is separated from the balance of the syngas. The condensed steam exits the methanol production unit or system via line 22.

Line 23 conveys the dehumidified syngas from the water knock out unit 21 to a hydrogen separation unit 24 wherein some of the syngas is separated into a hydrogen-rich stream 25 and a makeup syngas stream 29. The hydrogen separation unit 24 may be a membrane that is more permeable to hydrogen than to other species in the syngas or may be a different type of separating unit such as a distillation column or molecular sieve, for example. Line 25 conveys the hydrogen rich stream from the hydrogen separation unit 24 to a burner 26, which, in some embodiments, can be a recuperative burner. The hydrogen rich stream is preheated against combustion products exiting the furnace 15 and combusted with a preheated oxidant such as air to provide heat to the furnace 15.

Line 27 conveys ambient air to the burner 26 wherein the air is preheated against combustion products exiting the furnace 15 and is combusted with hydrogen from line 25 to form combustion products. Combustion products exit the furnace 15 via the burner 26 wherein they are cooled against hydrogen from line 25 and air from line 27. Line 28 conveys the cooled combustion products from the furnace 15. In some embodiments, the hydrogen rich stream can be sent to a storage unit for later sale or use, or can be a supply to another system for use in a separate application.

Line 29 conveys the makeup syngas stream from the hydrogen separation unit 24 to a compressor 30 wherein the makeup syngas is compressed. Line 31 conveys the compressed makeup syngas from the compressor 30 and return syngas feed from line 46 to a further compressor 32 wherein the combined feed is compressed. Line 33 conveys the compressed combined feed from compressor 32 to a heat exchanger 34 wherein the feed is heated against process gas in line 40. Line 35 conveys the heated feed from heat exchanger 34 to a methanol synthesis reactor 36 wherein some of the feed is converted to methanol over a catalyst.

The outlet from the methanol synthesis reactor is a mixture that can contain methanol, methane, CO, $CO_2$, $H_2$ (in relatively small amounts), and potentially other species. Line 37 conveys the outlet mixture containing methanol from the synthesis reactor to lines 38 and 39. Line 38 conveys some of the mixture from line 37 through heat exchanger 2 wherein the mixture is cooled against feedstock from line 1 and on to line 40. Line 39 conveys some of the mixture from line 37 through heat exchanger 10 wherein the mixture is cooled against the water from line 9 and on to line 40. Line 40 conveys the mixture from lines 38 and 39 to heat exchanger 34 wherein the mixture is cooled against feed from line 33. Line 41 conveys the cooled mixture from heat exchanger 34 to heat exchanger 42 wherein the mixture is further cooled. Line 43 conveys the cooled mixture from heat exchanger 42 to a distillation column 44 wherein the mixture is separated into a methanol-rich stream 45 and a methanol-poor stream 46. Line 45 conveys the methanol-rich stream to refining units wherein the methanol-rich stream is further refined to more highly concentrated methanol, or which is sent to a storage unit or for use in a separate application. The methanol poor stream can include carbon species, e.g., $CH_4$, CO, $CO_2$, that would be undesirable to release directly into the environment as greenhouse gases, or which would advantageously be used or sequestered.

Line 46 conveys a first portion of the methanol-poor stream or mixture from the distillation column 44 as recycle gas to line 31 wherein the recycle syngas mixes with the makeup syngas from compressor 30. Line 47 conveys a second portion of the methanol-poor stream from line 46 to an elevated pressure heater 48 wherein some of the second portion is heated, and to line 52.

The system can include a separation unit (not shown) to separate carbon containing species from non-carbon-containing species in methanol-poor line 47. For example, nitrogen, oxygen, and hydrogen gasses can be separated from carbon containing species. The nitrogen, hydrogen, oxygen, and non-carbon-containing species can be separated into line 52, and the carbon-containing species can be separated into line 49. Line 49 conveys the heated part of the second portion from the heater 48 to a turbo expander 50 wherein the mixture is expanded to perform work, such as on a shaft and generator 51. Line 65 conveys the expanded mixture from the turbo expander 50 to line 8 as recycle feed to the steam reforming reactor 14. The flow rate of the second tail gas stream 47 or SMR recycle stream can be adjusted to prevent the methane content of the tail gas from exceeding a predetermined concentration, for example, by using a valve, a throttle, a reducer, a flow constrictor, or other similar device.

Line 52 conveys a third portion of the methanol-poor stream from line 47 from the separation unit which separates non-carbon containing species, to a burner 53 such as a recuperative high-pressure burner wherein the remainder of the second portion is preheated against combustion products from the heater 48 and combusted with air from line 54. The flow rate of the third tail gas stream 52, constituting a nitrogen purge stream in some embodiments, can be adjusted to prevent the nitrogen content of the tail gas from exceeding a predetermined concentration. Line 55 conveys ambient air to a compressor 56 wherein the air is compressed. Line 54 conveys the compressed air from the compressor 56 to the burner 53 wherein the compressed air is heated against combustion products from heater 48 and combusted with the methanol-poor stream from line 52 to form combustion products. Combustion products formed in the burner 53 circulate through and exit the heater 48 through burner 53 wherein they are cooled against the methanol-poor stream from line 52 and compressed air from line 54. Line 57 conveys the cooled combustion products from the burner 53 to a carbon dioxide separation unit 58 such as a scrubber, wherein carbon dioxide is separated from the combustion products at elevated pressure. Line 59 conveys the separated carbon dioxide from the methanol production system.

Line 60 conveys decarbonized combustion products from the carbon dioxide separation unit to the heater 48 wherein they are heated. Line 61 conveys the heated decarbonized combustion products from the heater 48 to a turbo expander 62 wherein they are expanded to perform work, such as on a generator and shaft 63. Line 64 conveys the expanded decarbonized combustion products from the methanol production system.

The pressures in lines within the synthesis loop shown as dashed lines may in some embodiments be preferably greater than 50 bar. The pressures of the process gas lines shown as solid lines may in some embodiments be preferably greater than 20 bar. The pressures of lines 27, 28, 55, and 64, shown as dotted lines, may in some embodiments be preferably near ambient pressure.

Figure 2:
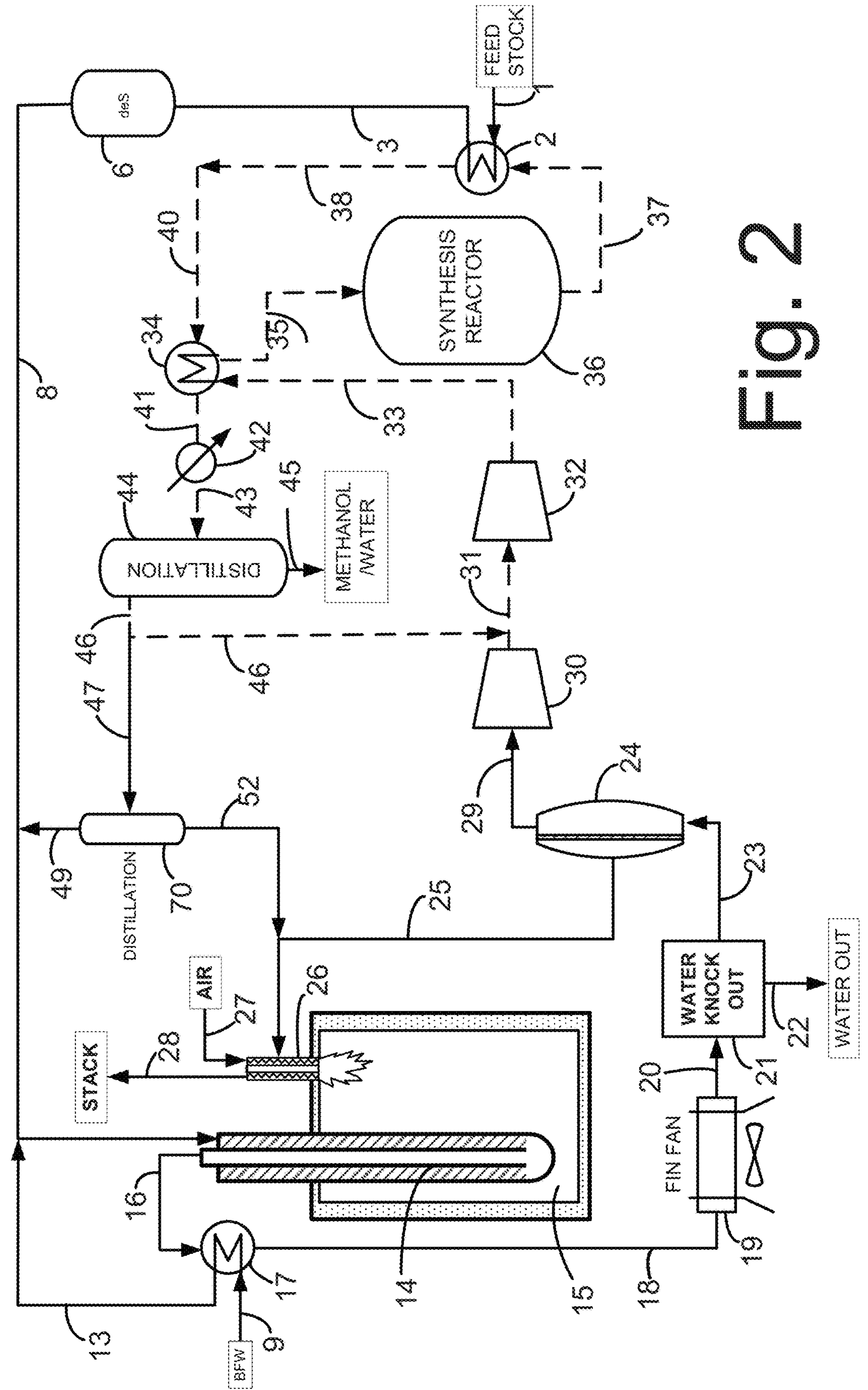
FIG. 2 schematically illustrates a methanol production unit in accordance with the present technology.

FIG. 2 depicts an embodiment of a methanol production unit implementing green methanol production. Some lines, components, and features of FIG. 2 can be similar to those described with regard to FIG. 1. Where lines and/or components can be similar, the same reference numbers have been used. Descriptions of FIG. 1 of similar components can apply to the components of FIG. 2.

In FIG. 2, line 1 conveys a hydrocarbon feedstock to a heat exchanger 2 wherein the feedstock is preheated against gas in line 37.

Line 3 conveys the preheated feedstock from the heat exchanger 2 to a desulphurization unit 6 wherein the feedstock is desulphurized. Line 8 conveys the desulphurized feedstock from the desulphurization unit 6.

Line 9 conveys boiler feed water to a boiler 17 wherein the boiler feed water is raised to steam against syngas in line 16. Line 13 conveys the steam from the boiler 17 to line 8 wherein the steam mixes with the feedstock from line 8 to form a mixed feed. Line 49 also mixes with line 8 and is part of the mixed feed. Discussion of the components of line 49 is below.

Line 8 conveys the mixed feed to a steam reforming reactor 14 wherein the mixed feed is converted to a syngas containing hydrogen and oxides of carbon. The steam reforming reactor 14 is heated by a furnace 15.

Line 16 conveys the syngas from the steam reforming reactor 14 to a heat exchanger 17, wherein the syngas is cooled against a stream 9. Although FIG. 2 illustrates the syngas in line 16 being cooled against stream 9, the hot syngas in line 16 can be used to heat any of streams 1, 3, 9, 11, 47, 60, 26, 54, or 33, or another stream or fluid. Line 18 conveys the cooled syngas from the heat exchanger 17 to a fin fan 19.

In fin fan 19, or other similar apparatus for cooling the syngas, the syngas is cooled against ambient air or water, and some of the steam in the syngas condenses. Line 20 conveys the cooled syngas to a water knock out unit 21 wherein the condensed steam (in the form of liquid water) is separated from the balance of the syngas. The condensed steam exits the system via line 22.

Line 23 conveys the dehumidified syngas from the water knock out unit 21 to a hydrogen separation unit 24 wherein some of the syngas is separated into a hydrogen-rich stream 25 and a makeup syngas stream 29. The hydrogen separation unit 24 may be a membrane that is more permeable to hydrogen than to other species in the syngas or may be a different type of separating unit such as a distillation column or molecular sieve, for example. Line 25 conveys the hydrogen rich stream from the hydrogen separation unit 24 to a burner 26, which, in some embodiments, can be a recuperative burner. The hydrogen rich stream is preheated against combustion products exiting the furnace 15 and combusted with a preheated oxidant such as air to provide heat to the furnace 15.

Line 27 conveys ambient air to the burner 26 wherein the air is preheated against combustion products exiting the furnace 15 and is combusted with hydrogen from line 25 to form combustion products. Combustion products exit the furnace 15 via the burner 26 wherein they are cooled against hydrogen from line 25 and air from line 27. Line 28 conveys the cooled combustion products from the furnace 15. In some embodiments, the hydrogen rich stream can be sent to a storage unit for later sale or use, or can be a supply to another system for use in a separate application.

Line 29 conveys the makeup syngas stream from the hydrogen separation unit 24 to a compressor 30 where the makeup syngas is compressed. Line 31 conveys the compressed makeup syngas from the compressor 30 and return syngas feed from line 46 (described below) to a further compressor 32 wherein the combined feed is compressed. Line 33 conveys the compressed combined feed from compressor 32 to a heat exchanger 34 wherein the feed is heated against process gas in line 40. Line 35 conveys the heated feed from heat exchanger 34 to a methanol synthesis reactor 36 wherein some of the feed is converted to methanol over a catalyst.

The outlet from the methanol synthesis reactor is a mixture that can contain methanol, methane, CO, $CO_2$, $H_2$ (in relatively small amounts), and potentially other species. Line 37 conveys the outlet mixture containing methanol from the synthesis reactor to line 38. Line 38 conveys the mixture from line 37 through heat exchanger 2 wherein the mixture is cooled against feedstock from line 1, and then on to line 40. Line 40 conveys the mixture from line 38 to heat exchanger 34 wherein the mixture is cooled against feed from line 33.

Line 41 conveys the cooled mixture from heat exchanger 34 to heat exchanger 42 wherein the mixture is further cooled. Line 43 conveys the cooled mixture from heat exchanger 42 to a distillation column 44 wherein the mixture is separated into a methanol-rich stream 45 and a methanol-poor stream 46. Line 45 conveys the methanol-rich stream to refining units wherein the methanol-rich stream is further refined to more highly concentrated methanol, or which is sent to a storage unit or for use in a separate application.

The methanol poor stream can include carbon species, e.g., $CH_4$, CO, $CO_2$, that would be undesirable to release directly into the environment as greenhouse gases, or which would advantageously be used or sequestered.

Line 46 conveys a first portion of the methanol-poor stream or mixture from the distillation column 44 as recycle gas to line 31 wherein the recycle syngas mixes with the makeup syngas from compressor 30.

Line 47 conveys a second portion of the methanol-poor stream from line 46 to separator 70 wherein the second portion is separated into a purge stream containing relatively higher concentration of nitrogen or other inert gases to the synthesis process and a SMR recycle stream containing relatively lower concentration of nitrogen or other inert species to the synthesis process. The separator may be of any kind, including a distillation column, adsorbent, or absorbent.

Line 49 conveys SMR recycle stream from separator 70 to line 8 wherein it mixes with desulphurized feedstock from unit 6. The SMR recycle gas may contain $CH_4$, CO, and/or $CO_2$.

Line 52 conveys the purge gas from separator 70 to line 25 wherein it combines with the hydrogen rich gas in line 25 and is conveyed as fuel to burner 26 wherein it is combusted. The purge gas may contain hydrogen and higher concentration of nitrogen and hydrogen gasses, but in which carbon containing species have been minimizes, reduced, or eliminated in separator 70.

Other advantages and other embodiments of the current invention will be obvious to those skilled in the art. Their omission here is not intended to exclude them from the claims advanced herein.

The process described herein can reduce, minimize, or eliminate the need to exhaust carbon to the environment or the requirements of a carbon scrubber. By recirculating the tail gas through the methanol synthesis unit and distillation column, unreacted carbon species from a first pass can be reacted in a second pass or subsequent pass through the methanol synthesis unit 36 and the distillation column, where the methanol can be separated and removed from the system. By recirculating some of the tail gas through the steam reforming unit, unreacted methane from a first pass can be reacted in a second pass or subsequent pass in the steam reforming unit 14. By releasing a purge gas from the system the accumulation of inert gases such as nitrogen can be managed.

Although the present invention has been described in terms of certain preferred embodiments, various features of separate embodiments can be combined to form additional embodiments not expressly described. Moreover, other embodiments apparent to those of ordinary skill in the art after reading this disclosure are also within the scope of this disclosure. Furthermore, not all the features, aspects and advantages are necessarily required to practice the present technology. Thus, while the above detailed description has shown, described, and pointed out novel features of the present technology as applied to various embodiments, it will be understood that various omissions, substitutions, and changes in the form and details of the apparatus or process illustrated may be made by those of ordinary skill in the technology without departing from the spirit or scope of the present disclosure. The present technology may be embodied in other specific forms not explicitly described herein. The embodiments described above are to be considered in all respects as illustrative only and not restrictive in any manner.

What is claimed is:

1. A method of producing methanol, the method comprising:

reforming a feed comprising steam and at least one hydrocarbon in a steam reforming reactor to produce a syngas comprising hydrogen and one or more oxides of carbon;

separating the syngas into a hydrogen-rich stream and a second stream in a hydrogen separation unit;

processing the second stream in a synthesis reactor to form an outlet stream comprising methanol;

separating the outlet stream into a methanol-rich stream and a methanol-poor tail gas stream;

recycling a first portion of the tail gas stream to the synthesis reactor;

separating a second portion of the tail gas stream into a steam reforming recycle stream having a relatively lower concentration of inert gases and a purge stream having a relatively higher concentration of inert gases;

adding the steam reforming stream to the feed to be reformed; and combusting the purge stream to heat the steam reforming reactor.

2. The method of claim 1 wherein the hydrogen separation unit comprises a membrane.

3. The method of claim 1, further comprising combusting at least a portion of the hydrogen-rich stream to provide heat to the steam reforming unit.

4. The method of claim 1, wherein the volume ratio of hydrogen to oxides of carbon in the second stream is between 1.8/1.0 and 2.8/1.0.

5. The method of claim 4, wherein the volume ratio of hydrogen to oxides of carbon in the second stream is approximately 2.5/1.0.

6. The method of claim 1, wherein a third portion of the tail gas stream is separated into a fuel stream.

7. The method of claim 6, further comprising combusting at least a portion of the fuel stream to form combustion products and to provide heat to the steam reforming unit.

8. The method of claim 7, wherein the combustion products contain carbon dioxide.

9. The method of claim 8, further comprising separating at least a portion of the carbon dioxide from the combustion products.

10. The method of claim 9, further comprising sequestering the separated carbon dioxide.

11. The method of claim 1, wherein the outlet stream is separated in a distillation column.

12. The method of claim 1, further comprising pressurizing the second stream in a compressor.

13. The method of claim 12, wherein the second stream enters the synthesis unit at a pressure greater than 50 bar.

14. The method of claim 1, further comprising preheating at least a portion of the feed against at least a portion of the outlet stream.

* * * * *